United States Patent
Hong

(10) Patent No.: US 7,830,503 B2
(45) Date of Patent: Nov. 9, 2010

(54) FLOWTHROUGH CELL OF THE FLOWING SPECTROPHOTOMATIC ANALYSIS

(76) Inventor: Lingcheng Hong, 19/F Jixie Mansion, No. 49 Zhongshan North Road, Nanjing (CN) 210008

( * ) Notice: Subject to any disclaimer, the term of this patent is extended or adjusted under 35 U.S.C. 154(b) by 163 days.

(21) Appl. No.: 12/295,509

(22) PCT Filed: Mar. 20, 2007

(86) PCT No.: PCT/CN2007/000899

§ 371 (c)(1),
(2), (4) Date: Sep. 30, 2008

(87) PCT Pub. No.: WO2007/112659

PCT Pub. Date: Oct. 11, 2007

(65) Prior Publication Data

US 2009/0046282 A1 Feb. 19, 2009

(30) Foreign Application Priority Data

Mar. 31, 2006 (CN) .......................... 2006 1 0039219

(51) Int. Cl.
*G01N 21/00* (2006.01)

(52) U.S. Cl. ....................................... 356/246; 356/440

(58) Field of Classification Search ................. 356/440, 356/246, 244; 250/227.25, 576; 422/82.05, 422/82.09

See application file for complete search history.

(56) References Cited

U.S. PATENT DOCUMENTS

| 4,008,397 | A | 2/1977 | Zdrodowski |
| 5,057,216 | A | 10/1991 | Chervet |
| 5,423,513 | A * | 6/1995 | Chervet et al. ......... 250/227.25 |
| 7,291,824 | B2 * | 11/2007 | Kiesel et al. ............. 250/208.2 |
| 7,403,280 | B2 * | 7/2008 | Beigel et al. ................. 356/246 |
| 7,641,856 | B2 * | 1/2010 | Padmanabhan et al. ....... 422/73 |
| 2005/0078308 | A1 * | 4/2005 | Gilby ......................... 356/246 |

FOREIGN PATENT DOCUMENTS

CN 2711732 7/2005

* cited by examiner

*Primary Examiner*—Hoa Q Pham
(74) *Attorney, Agent, or Firm*—The Webb Law Firm

(57) ABSTRACT

A transparent tube is used as the fluid pathway of a flowthrough cell, which not only makes sure the fluid can retain the stable laminar state without micro-bubble existing, but also can avoid the turbulent state and the micro-bubbles that produce the negative peak and the interference peak. Utilizing the transparent property of the pipe wall, the outer wall of both ends of the optical pathway is made to be a smooth plane and forms a single unit planar light inlet window with the pipe. The cell does not need to be furnished with a glass window or a quartz glass window any more. This design has solved the leakage and dead angle problems. The invention not only simplifies the structure but also increases the precision.

2 Claims, 2 Drawing Sheets

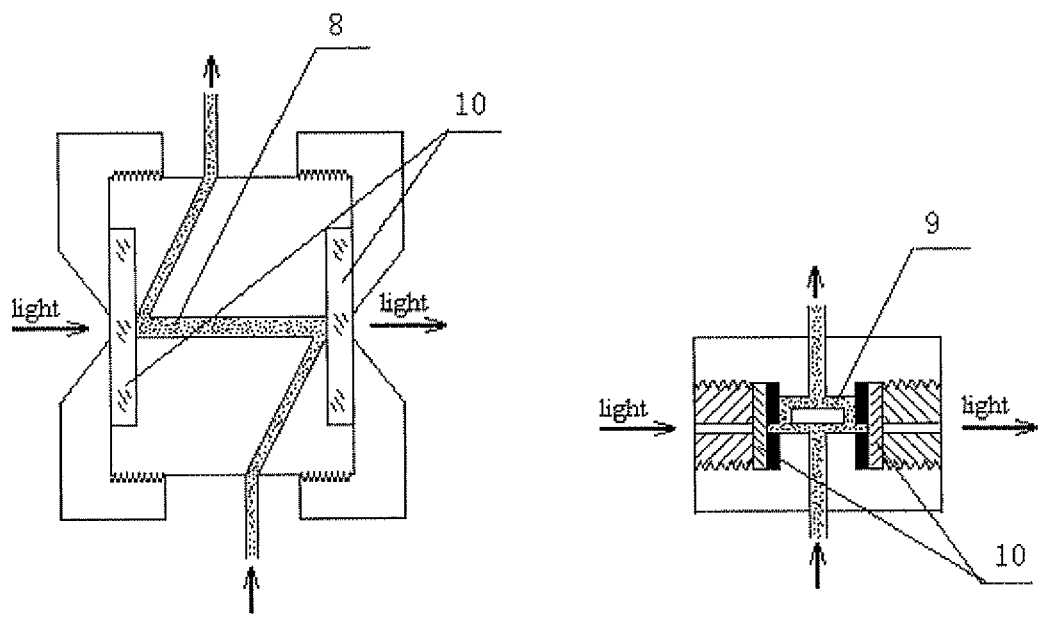
Fig. 1
Fig. 2
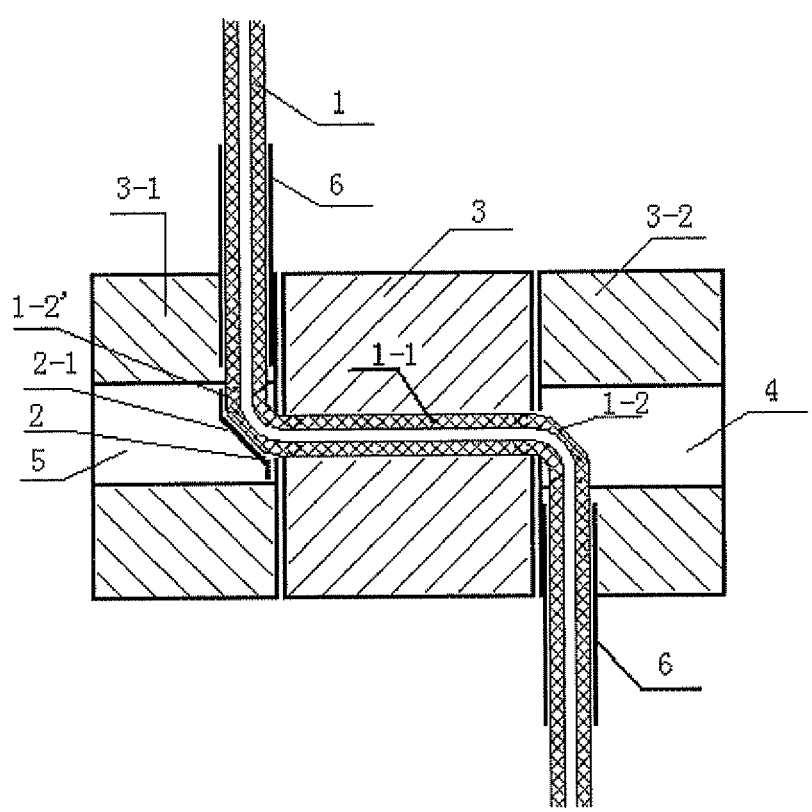
Fig. 3

FLOWTHROUGH CELL OF THE FLOWING SPECTROPHOTOMATIC ANALYSIS

BACKGROUND OF THE INVENTION

1. Field of the Invention

The invention involves a flow through cell that is a photometric detector for determining the chemical composition contents in fluid. Especially, it is used for photometric detection in the flowing station, which belongs to the chemical analysis instrument.

2. Background of Related Art

The flowing spetrophotomatic analysis is a channelization continuous flow analysis; the sample is injected into the carrier solution and reacts with the carrier solution or the reagent in the carrier solution. Subsequently, the sample flows into the detector with constant speed along the carrier solution. This method is simple, quickly analysis speeds, high precision, easy automation continuous analysis. Recently, it has shown a wide application in variety fields such as environments, clinic, medicines, agroforestry, metallurgical geology, industrial process monitoring, biochemistry, food; Furthermore, the photometric colorimeter with the flowthrough cell is used the most one of the photometric detectors in FIA.

The base of the cell is furnished with a fluid inlet and wastewater outlet, and there is a fluid pathway inside the base that connects with the above inlet and outlet. The fluid pathway includes two turns at least. The optical path locates between the optical entrance and optical exit, and its both ends locate in the turning position of the fluid pathway. According to the shape of fluid pathway, the traditional flowthrough is classified into Z-type (see FIG. 1), H-type (see FIG. 2) and U-type, etc. Regardless of the type, both ends of the optical pathway must have a quartz glass window or a glass window, while the fluid pathway is directly graved inside the base. When the fluid transporting tube connects with the base inlet, the fluid would flow out form the outlet along the base groove rail under the pump propelling and flow through the optical pathway. The fluid irradiated with light to detect in photometric analysis. The disadvantages of the current flowthrough cell are: ① the diameter of the flow transporting tube and optical path is inconsistent and there is a dead angle between the both ends of optical path which results in the state of fluid changing form original stable laminar to turbulent, furthermore which could produce refraction of light and display interference peak; If the interference peak affects the results seriously that will destroy the peak value to produce the measurement error; ② because of the poor smooth finish inner wall of the pathway, the micro-bubble in water could be detained and adsorbed on the pathway, which the micro-bubble is not to be discharged that could cause light scattering and false absorption to bring measurement error; ③ the glass window and quartz glass window occur the leakage easily under high pressure; Or because of the temperature changing, the expansion coefficient of material is different which could also cause the leakage; ④ the flow pathway utilizes multi-produce such as furrow, polish, etc. SO, that is complicated technology, very high precision requirement, high production cost and has difficult in meet the accuracy requirement. Presently, the method has never been found to solve the above defects of traditional flow pathway. Especially, the limitation is distinct when the flowthrough cell is used to detect the strong corrosive and strong oxidative fluid.

SUMMARY OF THE INVENTION

The invention aims to provide a new flowthrough cell to overcome the above defects. It has some advantages such as no micro-bubble detaining, no interference peaks, no leaking, precise and credible.

In this invention, the flowthrough cell is furnished with a base with an entrance and exit of light. The character of the invention is that a transparent tube is used as the fluid pathway inside the base. Both ends of the transparent tube jut out form the base, one end is used to be the fluid transporting tube, the other end is used to be the wastewater outlet tube; the transporting tube includes two transitional circular arc turns at least. The light pathway is a segment straight tube with turns at the both ends, and the light pathway locates between the optical entrance and exit. The outer wall of the turns with the transparent tube form a planar light inlet window, the so-called transparent tube pass through the prefabricated groove rail or pore channel positioning in the base.

The lucite pipe, transparent glass pipe and transparent quartz glass pipe can be selected as the transparent tube, such as polytetrafluoroethylene (PTFE), polyethylene (PE) and polycinychloride (PVC), etc.

The diameter of the transparent tube should near or the same to the transporting pipe of the flowing analysis. That makes the diameter and the shape of the pipe have no great change before entering into the cell, so the fluid not only can keep the original speed and laminar state, but also on occurring the refraction of light and no the interference peak affects the findings.

If the fluid entrance end pipe that juts out from the base has an appropriate length, the fluid would be steady flow before flowing into the optical pathway. In spite of the diameter is great difference between transparent tube and capillary, the fluid still keeps on the laminar state.

In this invention, the transparent tube is used as the fluid pathway in order to make sure the inner surface of the pathway is smooth, so the micro bubble would not to be detained. The circular arc is used as the transitional form of the turn in the base to make sure the turn is smooth and no dead angle exiting so that the fluid could turn steadily and keep on the laminar state rather than the unstable turbulent; the whole course of flowing is the stable laminar that make sure no interference peak and negative peak existing, so the finding of the research is accurate. Parallelled with the traditional flowthrough cell, the new simplifys the manufacture greatly, though the base is furnished with the groove rail and the pore channel, these are only used as the orientation of the transparent tube rather than the flowthrough cell directly. Therefore, there is no strict requirement for the size and the smooth finish so that the cost is decreased greatly. The optical pathway of the flowthrough cell is a segment straight pipe of the holistic plastic tube, Utilizing the transparent property of the pipe wall, the outer wall of both ends of the optical pathway is made to be a smooth plane and forms a single unit planar light inlet window with the pipe. There do not need to be furnished with the glass window or the quartz glass window any more. The structure of the flowthrough cell is simple that has solved the leakage problem completely.

Conclusion: in the invention, the transparent tube is used as the fluid pathway of the flowthrough cell, which not only makes sure the fluid can retain the stable laminar state and no micro-bubble existing, but also can avoid the turbulent and the micro-bubble producing the negative peak and the interference peak, Utilizing the transparent property of the pipe wall, the outer wall of both ends of the optical pathway is made to be a smooth plane and forms a single unit planar light inlet window with the pipe, There do not need to be furnished with the glass window or the quartz glass window any more, This smart design has solved the leakage and dead angle problem that have puzzled people for a long term. The invention not only simplifies the structure but also increases the precision. It produces an unexpected research finding.

BRIEF DESCRIPTION OF THE DRAWINGS

FIG. 1, FIG. 2 is the structure schematic diagram of traditional Z-type and H-type flowthrough cell, respectively.

FIG. 3 is the structure schematic diagram of the Z-type flowthrough cell of the invention.

DETAILED DESCRIPTION

Figure 4:
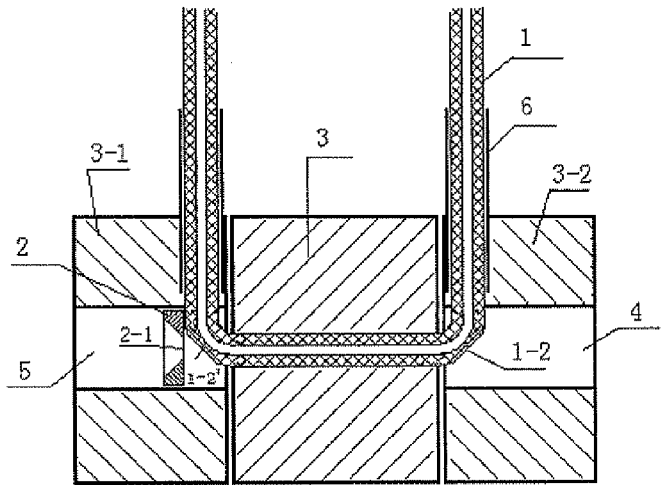
FIG. 4 is the structure schematic diagram of the U-type flowthrough cell of the invention.

In the diagram, 1—the transparent tube, 1-1 the optical pathway, 1-2, 1-2'—the planar light inlet window, 2—the oillet of the limiting optical tablet, 3—the base, 3-1—the left end cap of the base, 3-2—the right end cap of the base, 4—the incident light entrance port, 5—the emergent light exit port, 6—black bushing, 8—the traditional Z-type pathway, 9—the traditional H-type pathway, 10—the quartz glass window.

FIG. 1 is the traditional Z-type flowthrough cell, the flow pathway is graved on the base in the form of Z-type (8), the fluid flows into the cell from one end to the other end. On the both sides of the flowthrough cell is the glass window or the quartz glass window (10), it is sealed by the polytetrafluoroethylene gasket.

FIG. 2 is the traditional H-type flowthrough cell, the flow pathway is graved on the base in the form of H-type (9). The flow path would be divided into two paths after the fluid flows into the cell from the underside middle of the cell, and then the fluid would accord to opposite direction to reach the window. Later the opposite fluids are beginning to converge, and the fluid flow out form the upside middle of the cell. On the both sides of the flowthrough cell is the glass window or the quartz glass window (10), it is sealed by the polytetrafluoroethylene gasket.

Seen from the above two figures, the both ends of the traditional flowthrough cell needs to be furnished with a quartz glass window or a glass window (10) and sealed by the polytetrafluoroethylene gasket, its structure is complex so that it produces leakage easily. Besides that all of the pathways are graved on the base directly, the inner wall must be polished, kept cleaning when used, high requirement of the manufacture technology is demanded.

The Example 1

The Z-Type Flowthrough Cell of the Invention

FIG. 3 shown: the flowthrough cell comprises the base(3), the left end cap (3-1) and the right end cap (3-2). In this example, the transparent plastic tube (1) has two turns in the base in the form of Z-type; between the turn ends is the optical pathway (1-1) that locates between the light entrance and the exit. The outer wall of two turns of optical pathway (1-1) is grinded to be oblique planes 1-2, 1-2', which forms a single unit plane with the holistic tube. The plane is used as the entrance window and exit window of the light. There is a limiting optical tablet (2) in front side of the exit window (1-2'), the pore size of the oillet on the limiting optical tablet is corresponding to the internal diameter of the optical pathway (1-1). The both ends of the transparent tube jut out downward or upward form the base, respectively. On the flowthrough cell running, the fluid flows into the cell form lower end of the transparent tube 1, while the wastewater flows out form the upper end. When the fluid (carrying the sample) flows through the optical pathway would be irradiated with light, to detect the change value of photoelectric detector and the peak height would be obtained, now could calculate the content of a certain component. In order to avoid the bypass light interfering with the optical pathway 1-1, a black bushing (6) is added on the entrance and exit to the base, respectively. Winding the pipe of the black bushing one lap (or knotting), making sure that the light can not enter into the optical pathway along the transparent tube to interference with detection.

The Example 2

The U-Type Flowthrough Cell of the Invention

FIG. 4 shown: the structure of the U-type flowthrough cell is the same to the example 1, the difference of the invention is the transparent tube (1) takes on an U-type turn in the base, both ends of the end tube jut out upward form the base and the extension end is set up a black bushing (6). The plane has an angle betweens the limiting optical tablet (2) and the light inlet window, but the oillet is corresponding to the axis of optical pathway.

The Example 3

The Multi-Bend Type Flowthrough Cell of the Invention

Figure 5:
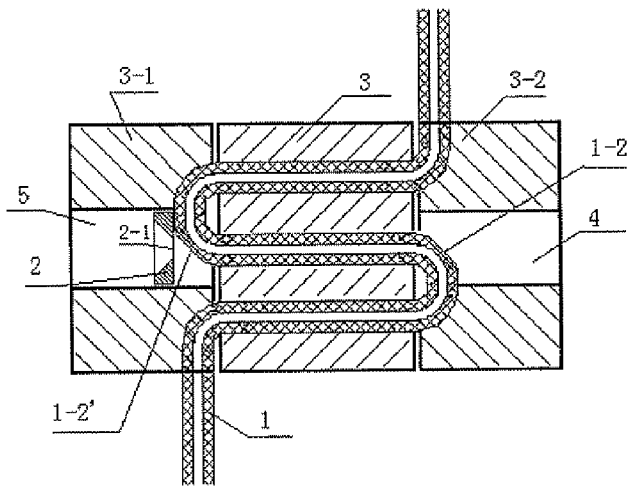
FIG. 5 is the structure schematic diagram of the multi-bent type flowthrough cell of the invention.
Figure 6:
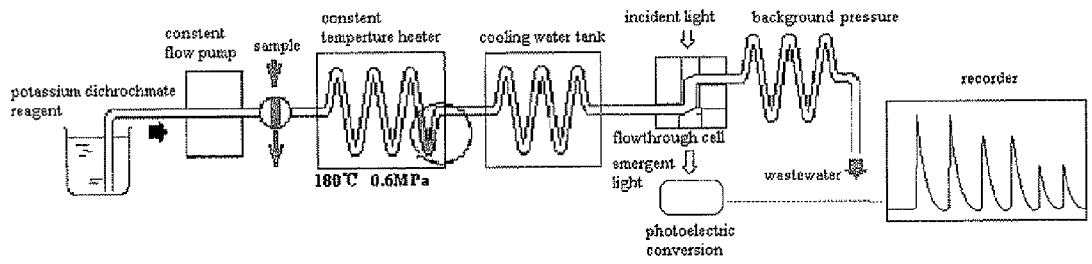
FIG. 6 is the flow chart of the FIA-spetrophotomatic analysis for the determination of COD in water.

FIG. 5 shown: the structure is the same to the example 1, the difference of the invention is that there are six turns in the base. In the example, the tube juts out from the base not only need not to be added the black bushing but also not to be knot. Because of tube had turned many times, the ray could not interference with the optical pathway at the entrance or exit.

FIG. 3~FIG. 5 shown: the positioning of the transparent tube in the base.

The Example 4

To Detect the Content of COD in Water by FIA-Septrophotomatic Analysis Flowthrough Cell Seen form the figure, the dilute sulfuric acid that contains potassiurndichromate is used as the carrier and transported into the reaction pipe (diameter 0.8 mm) by the ceramic constant flow pump. When the sample is injected into the reaction pipe by the injector, the sample would be propelled by the carrier and diffuse gradually in the driving process; the sample mixes with reagent in the form of gradient, then the gradient mixing belt passes through the constant temperature heater. Under the high temperature (180° C.) and 0.6 MPa pressure, the impurity reacts with the reagent quickly; Until the temperature is lower to normal temperature by the cooling water tank, the fluid would pass through the cell; the wastewater flows out form exit of the cell through the background pressure. When the fluid flows through the cell, it would be irradiated with light and the $C_r^{6+}$ would have a strongly absorbed at 380 nm while the optical single could change into the electric single; Recording the changed value to obtained the corresponding curves of the peak width and peak height. Consequently, the content of COD could be obtained.

The invention claimed is:

1. A flowthrough cell comprising:

a base with a light entrance and a light exit;

a prefabricated groove channel positioned in the base; and a fluid pathway inside the base, wherein a transparent tube is used as the fluid pathway, the transparent tube having a first end for inputting fluid into the cell and a second end for outputting wastewater from the cell, wherein the transparent tube is disposed along the prefabricated groove channel positioned in the base, the first end and the second end of the transparent tube extending from the base, wherein the transparent tube makes at least two transitional circular arc turns, an outer wall of two turns of the transparent tube is grinded to define oblique planes that form a single unit plane with the tube, the planes defining a light entrance window and a light exit window, wherein a straight portion of the transparent tube disposed between turns forms a light pathway, the light pathway is located between the light entrance and the light exit, and wherein the diameter of the transparent tube is near to or the same as the diameter of a pipe transporting the fluid through a flowing analysis.

2. The flowthrough cell of claim 1, wherein the transparent tube is selected from the group consisting of: Lucite pipe, transparent glass pipe, transparent quartz glass pipe, and transparent plastic pipe.

* * * * *